US011796781B2

(12) United States Patent
de Juan et al.

(10) Patent No.: US 11,796,781 B2
(45) Date of Patent: Oct. 24, 2023

(54) VISUALIZATION DEVICES, SYSTEMS, AND METHODS FOR OTOLOGY AND OTHER USES

(71) Applicant: Spiral Therapeutics Inc., Brisbane, CA (US)

(72) Inventors: Eugene de Juan, Brisbane, CA (US); Signe Erickson, Brisbane, CA (US); Vrad Levering, Brisbane, CA (US)

(73) Assignee: Spiral Therapeutics Inc., South San Francisco, CA (US)

(*) Notice: Subject to any disclaimer, the term of this patent is extended or adjusted under 35 U.S.C. 154(b) by 137 days.

(21) Appl. No.: 17/155,580

(22) Filed: Jan. 22, 2021

(65) Prior Publication Data

US 2021/0231935 A1 Jul. 29, 2021

Related U.S. Application Data

(60) Provisional application No. 63/082,996, filed on Sep. 24, 2020, provisional application No. 63/081,015, (Continued)

(51) Int. Cl.
*G02B 21/00* (2006.01)
*G02B 21/22* (2006.01)
(Continued)

(52) U.S. Cl.
CPC .......... *G02B 21/0012* (2013.01); *A61B 1/018* (2013.01); *A61B 1/227* (2013.01);
(Continued)

(58) Field of Classification Search
CPC ............... G02B 21/00; G02B 21/0004; G02B 21/0008; G02B 21/0012; G02B 21/0016;
(Continued)

(56) References Cited

U.S. PATENT DOCUMENTS 4,335,713 A 6/1982 Komiya
5,421,818 A 6/1995 Arenberg
(Continued)

FOREIGN PATENT DOCUMENTS

WO WO 1994010596 5/1994
WO WO 2008097317 8/2008
(Continued)

OTHER PUBLICATIONS

International Preliminary Report on Patentability in International Appln. No. PCT/US2021/014609, dated Aug. 4, 2022, 8 pages.
(Continued)

*Primary Examiner* — Thong Q Nguyen
(74) *Attorney, Agent, or Firm* — Fish & Richardson P.C.

(57) ABSTRACT

Devices, systems, and methods can be employed to facilitate indirect viewing into cavities such as, but not limited to, the middle ear space. Some embodiments have uses such as, but not limited to, facilitating visualization and procedures in the outer, middle, and/or inner ear in order to diagnose and/or treat disorders including, but not limited to, hearing loss and other ear disorders. In particular implementations, a surgical microscope is used in conjunction with an inverter lens and a distal lens. In some cases, the distal lens transverses a membrane or septum such as, but not limited to, the tympanic membrane. The distal lens can be an assembly combining two or more lenses, in some embodiments. For example, in some cases wide angle lenses, zoom lenses, lenses of other various shapes and/or prisms can be used in the distal lens.

24 Claims, 11 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.

| | | |
|---|---|---|
| *A61B 1/018* | (2006.01) | |
| *A61B 1/227* | (2006.01) | |
| *A61B 17/29* | (2006.01) | |
| *A61M 31/00* | (2006.01) | |
| *A61B 17/34* | (2006.01) | |
| *A61M 37/00* | (2006.01) | |
| *A61B 17/32* | (2006.01) | |
| *A61B 18/04* | (2006.01) | |
| *A61B 18/20* | (2006.01) | |
| *A61F 2/958* | (2013.01) | |
| *A61B 17/3205* | (2006.01) | |
| *A61B 18/14* | (2006.01) | |
| *A61F 11/20* | (2022.01) | |
| *A61B 17/00* | (2006.01) | |
| *A61B 18/00* | (2006.01) | |
| *A61F 2/18* | (2006.01) | |

(52) U.S. Cl.
CPC ......... *A61B 17/29* (2013.01); *A61B 17/3205* (2013.01); *A61B 17/320068* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(58) Field of Classification Search
CPC ............ G02B 21/0028; G02B 21/0032; G02B 21/02; G02B 21/025; G02B 21/06; G02B 21/20; G02B 21/22; G02B 21/361

USPC .................................................. 359/368–398
See application file for complete search history.

(56) References Cited

U.S. PATENT DOCUMENTS

| | | | |
|---|---|---|---|
| 6,024,726 | A | 2/2000 | Hill |
| 6,045,528 | A | 4/2000 | Arenberg et al. |
| 6,120,484 | A | 9/2000 | Silverstein |
| 6,440,102 | B1 | 8/2002 | Arenberg et al. |
| 6,648,873 | B2 | 11/2003 | Arenberg et al. |
| 7,351,246 | B2 | 4/2008 | Epley |
| 7,704,259 | B2 | 4/2010 | Kaplan et al. |
| 8,197,461 | B1 | 6/2012 | Arenberg et al. |
| 9,352,084 | B2 | 5/2016 | Decker et al. |
| 9,616,207 | B2 | 4/2017 | Verhoeven et al. |
| 10,098,529 | B2 * | 10/2018 | Gao ........................ G02B 9/06 |
| 10,130,514 | B2 | 11/2018 | Imran et al. |
| 10,492,670 | B1 | 12/2019 | Bendory et al. |
| 2003/0220536 | A1 | 11/2003 | Hissong |
| 2004/0133099 | A1 | 7/2004 | Dyer et al. |
| 2004/0172005 | A1 | 9/2004 | Arenberg et al. |
| 2004/0263958 | A1 | 12/2004 | Bihr et al. |
| 2011/0152621 | A1 * | 6/2011 | Magalhaes Mendes ..................... A61B 1/227 600/200 |
| 2011/0224629 | A1 | 9/2011 | Jolly et al. |
| 2012/0203200 | A1 | 8/2012 | Kenney et al. |
| 2013/0060131 | A1 | 3/2013 | Oghalai et al. |
| 2013/0245569 | A1 | 9/2013 | Jolly et al. |
| 2013/0267783 | A1 * | 10/2013 | Davis .................... A61B 1/227 600/199 |
| 2016/0346511 | A1 | 12/2016 | Cohen et al. |
| 2017/0172804 | A1 | 6/2017 | Watanabe et al. |
| 2019/0015254 | A1 | 1/2019 | Bendory et al. |
| 2019/0321610 | A1 | 10/2019 | Goldfarb et al. |
| 2020/0094030 | A1 | 3/2020 | Kim et al. |

FOREIGN PATENT DOCUMENTS

| | | |
|---|---|---|
| WO | WO 2019116024 | 6/2019 |
| WO | WO 2019152866 | 8/2019 |
| WO | WO 2019200259 | 10/2019 |
| WO | WO 2020115674 | 6/2020 |

OTHER PUBLICATIONS

PCT International Search Report and Written Opinion in International Appln. No. PCT/US2021/014609, dated Apr. 8, 2021, 10 pages.

Ent4Kids.co, "Microscopic Examination & Procedures," Ent4kids, retrieved on May 8, 2023, retrieved from URL<https://www.ent4kids.co.uk/pagem>, 3 pages.

Zeiss, "Zeiss Surgical Microscopes," Ent4kids, retrieved on May 8, 2023, retrieved from URL<https://www.zeiss.com/meditec/en/products/surgical-microscopes.html#ent-surgery>, 12 pages.

* cited by examiner

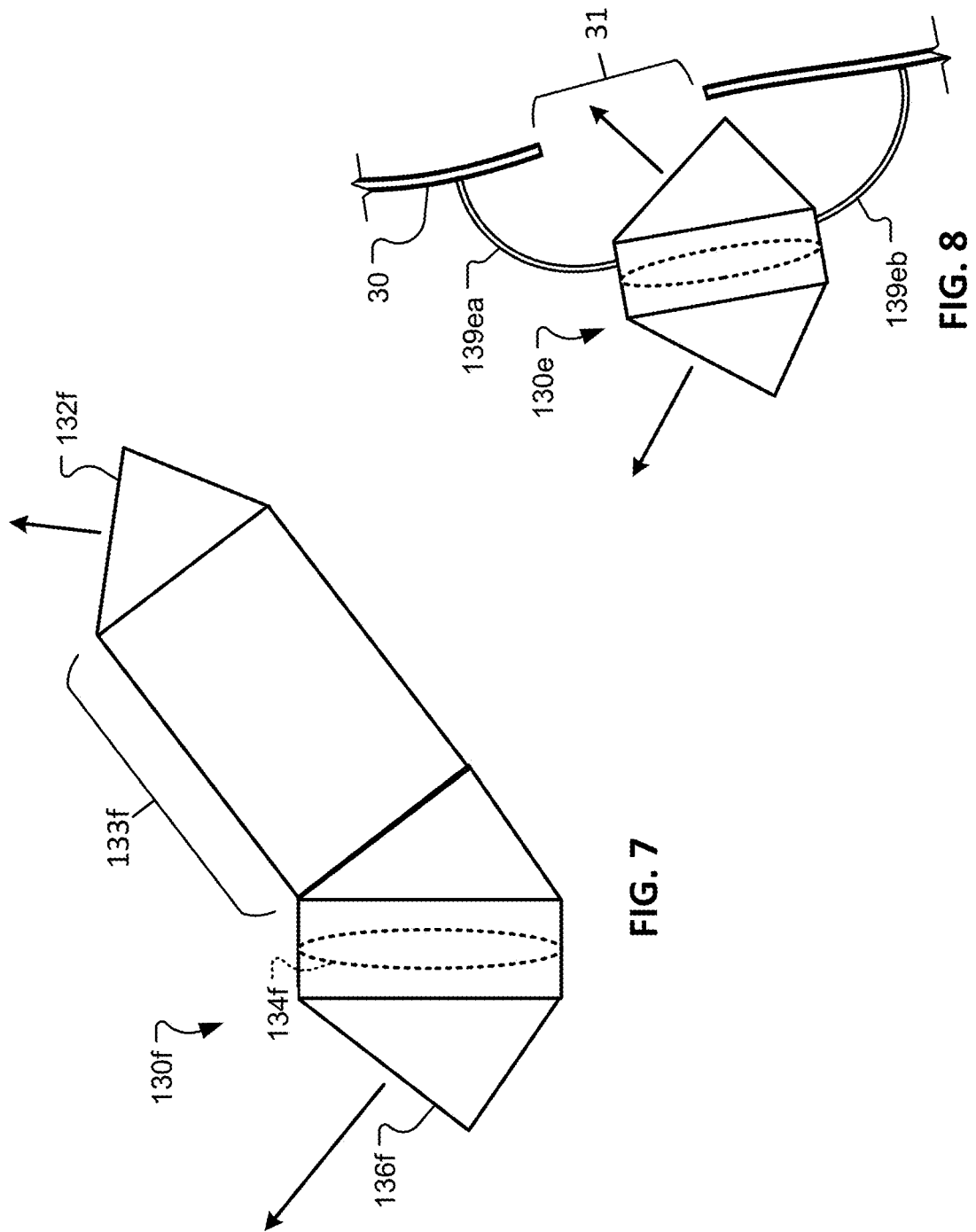

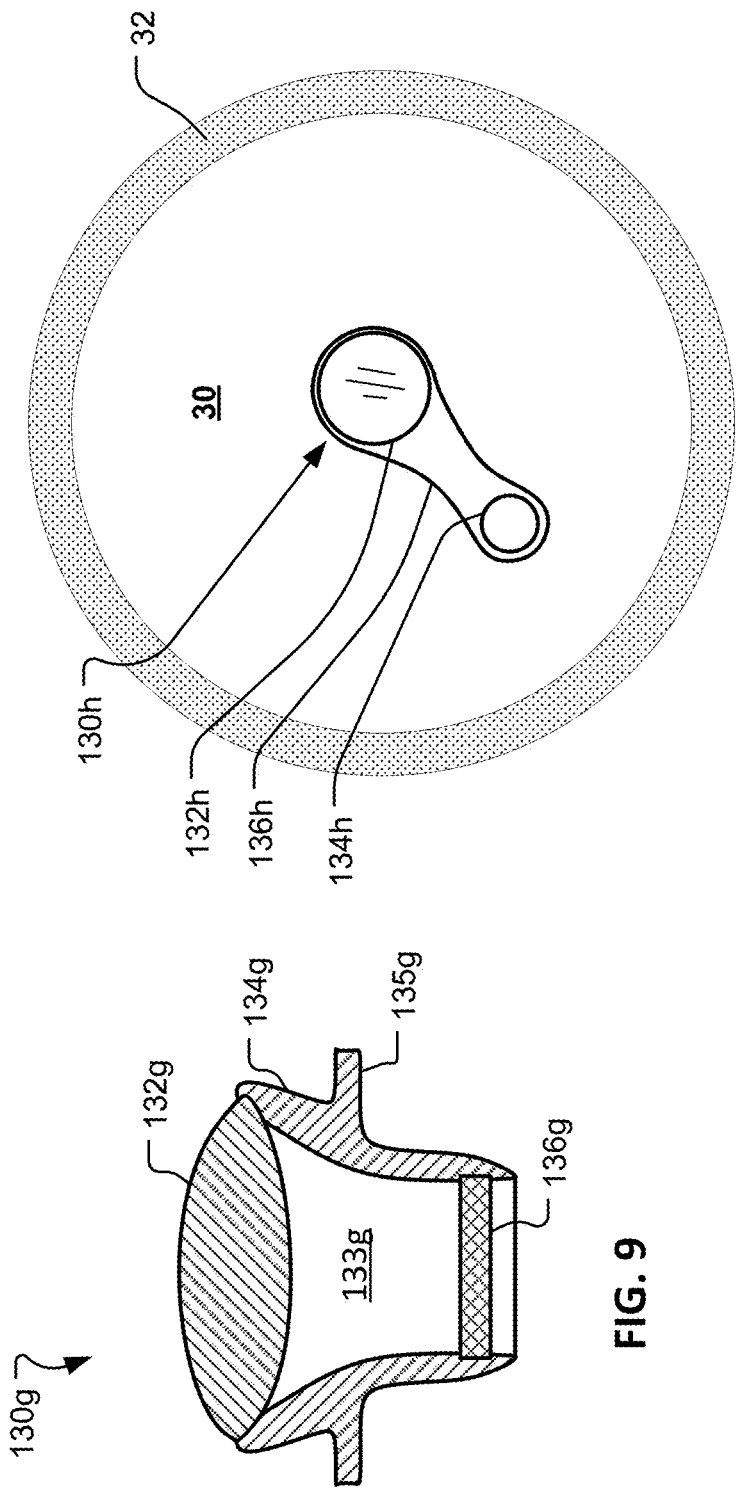

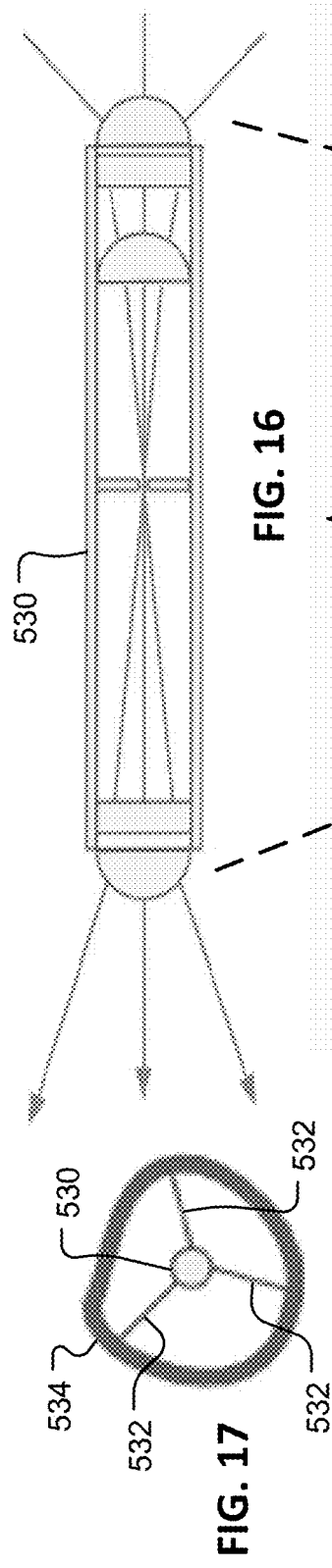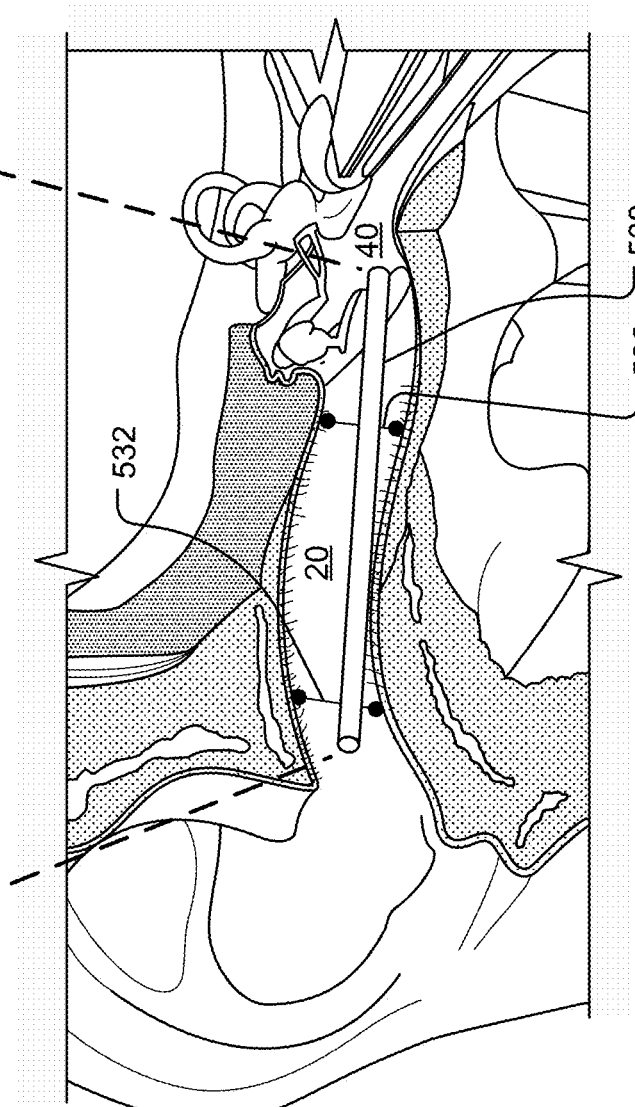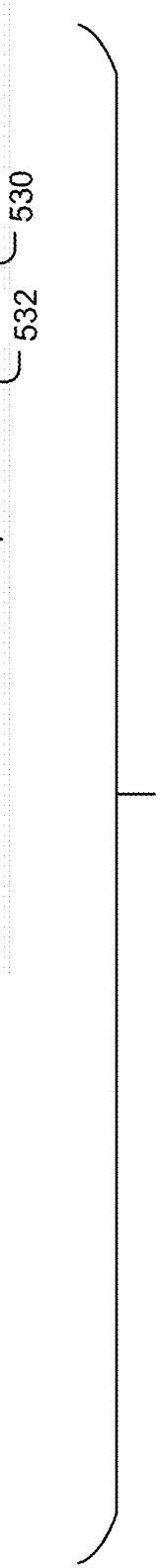
FIG. 15
FIG. 16
FIG. 17

VISUALIZATION DEVICES, SYSTEMS, AND METHODS FOR OTOLOGY AND OTHER USES

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020 (which is fully incorporated herein by reference), U.S. Provisional Application No. 63/040,495 filed on Jun. 17, 2020 (which is fully incorporated herein by reference), U.S. Provisional Application No. 63/051,568 filed on Jul. 14, 2020 (which is fully incorporated herein by reference), U.S. Provisional Application No. 63/077,448 filed on Sep. 11, 2020 (which is fully incorporated herein by reference), U.S. Provisional Application No. 63/078,141 filed on Sep. 14, 2020 (which is fully incorporated herein by reference), U.S. Provisional Application No. 63/080,510 filed on Sep. 18, 2020 (which is fully incorporated herein by reference), U.S. Provisional Application No. 63/081,015 filed on Sep. 21, 2020 (which is fully incorporated herein by reference), and U.S. Provisional Application No. 63/082,996 filed on Sep. 24, 2020 (which is fully incorporated herein by reference).

TECHNICAL FIELD

This document relates to devices, systems, and methods for facilitating visualization and procedures in the outer, middle, and inner ear in order to diagnose and/or treat disorders including, but not limited to, hearing loss and other ear disorders. In some examples, the systems and methods include instruments and techniques that facilitate indirect viewing into cavities such as, but not limited to, the middle ear space.

BACKGROUND

The human ear is subject to a variety of disorders including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, outer ear infections, middle ear infections, schwannoma, and tympanic membrane perforations, to provide a few examples.

In one example, Conductive Hearing Loss (CHL) involves the loss of normal mechanical pathways for sound to reach the hair cells in the cochlea, for example due to malformation, accumulation of fluid in the middle ear, disruption of the tympanic membrane, presence of tumors, and/or damage to ossicles. Sensorineural Hearing Loss (SNHL) is due to the absence of, or damage to, hair cells in the cochlea, or to the acoustic nerve. SNHL is typically associated with exposure to loud noise, head trauma, aging, infection, Meniere's Disease, tumors, ototoxicity, genetic diseases like Usher's disease, and the like.

While the use of endoscopes has increased over the last few years, and is in large part appealing because it allows wide angle viewing into the middle ear and adjacent spaces, endoscope use requires one of the surgeon's hands to operate, and typically removes binocularity which makes it difficult to assess depth, which then makes procedures more challenging and potentially damaging considering the delicate structures in the middle ear.

SUMMARY

This document describes devices, systems, and methods for uses such as, but not limited to, facilitating visualization and procedures in the outer, middle, and/or inner ear in order to diagnose and/or treat disorders including, but not limited to, hearing loss and other ear disorders. For example, this document describes devices, systems and methods that include instruments and techniques to facilitate indirect viewing into cavities such as, but not limited to, the middle ear space.

In particular implementations, a surgical microscope is used in conjunction with an inverter lens (which can include one or more lenses) and a distal lens (which can include one or more lens). In some embodiments, the inverter lens is located external to the body, such as external to the ear. In particular embodiments, the inverter lens is located within the body, such as within the ear canal. In certain embodiments, a portion of the inverter lens is external to the body and another portion of the inverter lens is located within the body.

In some cases, the distal lens traverses a membrane or septum such as, but not limited to, the tympanic membrane ("TM"). In particular cases, the distal lens is located in a way to enable visualization through an opening in a membrane or septum such as, but not limited to, the TM. In some embodiments, the distal lens can be an assembly combining two or more lenses. For example, in some cases wide angle lenses, zoom lenses, lenses of various shapes, and/or prisms can be used in the distal lens, as described further below. In addition, light fibers can be used to transmit images in some embodiments.

While the devices, systems, and methods for facilitating visualization and procedures are described herein in the example context of visualizing the middle ear and/or inner ear via the outer ear, it should be understood that the inventive concepts described herein are not limited to such a use. For example, in some embodiments the devices, systems, and methods for facilitating visualization and procedures described herein can be used for other middle ear and/or inner ear approaches such as, but not limited to, trans-mastoid access, trans-canal via tympanomeatal flap, endaural, retroaural, postaural, and others. Moreover, the devices, systems, and methods for facilitating visualization and procedures described herein are well-suited for use in other cavities or spaces in the body and other approaches, in addition to middle ear and/or inner ear visualization. For example, the devices, systems, and methods are well-suited for visualization and procedures pertaining to the eustachian tube, mastoid antrum space, and others.

The devices, systems, and methods described herein can be used in conjunction with additional treatment techniques. For example, the devices, systems, and methods described herein can be used in conjunction with treatment techniques such as, but not limited to, therapeutic agent delivery (which can be in the form of a gel, liquid, or solid), antibiotic delivery, gene delivery, device or implant delivery, diagnostic procedures, and surgical procedures, among others.

In some aspects, this disclosure is directed to a surgical microscope system that includes a surgical microscope, a stereoscopic inverter lens system, and a distal lens.

Such a surgical microscope system may optionally include one or more of the following features. The distal lens may be sized for placement in a tympanic membrane to facilitate visualization of a middle ear region. The distal lens may include a prism at a proximal end of the distal lens. The distal lens may include a widefield lens at a distal end of the distal lens. The distal lens may include a zoom or objective lens disposed between the prism and the widefield lens. The distal lens may define a waist having a smaller outer diameter than immediately adjacent proximal and distal portions of the distal lens. In some embodiments, the distal lens includes a first prism at a proximal end of the distal lens, and a second prism at a distal end of the distal lens. Such a distal lens may also include a zoom or objective lens disposed between the first and second prisms. In some embodiments, the distal lens comprises two or more stabilization arms extending radially outward from a body of the distal lens. In particular embodiments, the distal lens includes a condenser lens at a proximal end of the distal lens and coupled to a housing, and a second lens at a distal end of the distal lens and coupled to the housing. The housing may define an interior space between the condenser lens and the second lens. The interior space may be filled with a gas. The interior space may be filled with a liquid. The housing may include a radially extending flange or arms. In some embodiments, the system also includes a port device attached to the distal lens. In some embodiments, at least a portion of the stereoscopic inverter lens system is mounted within a speculum. In particular embodiments, the portion of the stereoscopic inverter lens system mounted within the speculum is positionally adjustable with respect to the speculum. An open space may be defined within the speculum and lateral of the portion of the stereoscopic inverter lens system mounted within the speculum. In some embodiments, the system also include a light pipe coupled to the distal lens. The distal lens may include an elongate tubular member and multiple lenses coupled to the tubular member to define a light path through the tubular member. Such a tubular member may include multiple sections that allow angularity between the sections. In some embodiments, the distal lens includes an elongate tubular member enclosing fiber optic fibers configured to relay images from a distal end of the distal lens to a proximal lens of the distal lens.

In additional aspects, this disclosure is directed to a method for indirect viewing into a middle ear space of a patient. The method includes providing a surgical microscope system comprising: (i) a surgical microscope; (ii) a stereoscopic inverter lens system; and (iii) a distal lens. The method also includes placing the distal lens in contact with a tympanic membrane of the patient, and viewing images of the middle ear space captured by the distal lens and relayed to the surgical microscope by the stereoscopic inverter lens system.

Such a method for indirect viewing into a middle ear space of a patient may optionally include one or more of the following features. The stereoscopic inverter lens system may be external to an ear of the patient. The stereoscopic inverter lens system may be within an ear canal of the patient. The method may include the use of the surgical microscope system with any of the embodiments and/or features described herein, in any combination.

Some or all of the embodiments described herein may provide one or more of the following advantages. First, current visualization of the middle ear space, inner ear, and nearby regions is challenging due to the constraints of access path, commonly either directly via the ear canal, via the canal through retroauricular transmeatal access created by invasively lifting the pinna, or through highly invasive transmastoid access created using bone drill and other instruments. In such situations, it is challenging to view around complex and delicate structures that create shadows and blind corners that still have to be navigated around for many procedures. Additionally, the access path is small in diameter, either due to the native dimensions and curvature of the ear canal, or due to the desire to minimize bone and tissue removal such as during trans-mastoid access. The use of a surgical microscope system, as described herein, has the benefits of allowing binocular viewing, and largely hands free operation by the surgeon.

Second, the use of a surgical microscope system for visualizing the middle and/or inner ear, as described herein, provides the additional advantages of allowing surgeons to utilize surgical microscopes that they are comfortable with, to be able to easily view down the ear canal in the manner that a surgical microscope is typically used, and to easily switch to a widefield view within the middle ear (e.g., to achieve view within view). Moreover, the surgical microscope systems described herein provide a large depth of focus and high resolution in the periphery.

Third, the devices, systems, and methods described herein advantageously allow the ability to pass instruments to the operative field, and to function in fluid-filled spaces in addition to air-filled spaces.

Fourth, the devices, systems, and methods described herein facilitate treatments in a minimally invasive fashion. Such minimally invasive techniques can tend to reduce recovery times, patient discomfort, recurrence of the disease, surgical complications, and treatment costs. Moreover, the methods described herein can be performed using a local anesthetic rather than requiring general anesthesia. Accordingly, the treatment cost, patient risks, and recovery times are further advantageously reduced.

Fifth, the systems described herein can also be used for diagnostic purposes. Such uses can help in procedure planning, change site of care, and potentially improve patient outcomes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 illustrates another example distal lens assembly that can be included as part of some embodiments of the surgical microscope system of FIG. 1.

FIG. 8 illustrates another example distal lens assembly that can be included as part of some embodiments of the surgical microscope system of FIG. 1. The distal lens assembly is illustrated as adjacent to an opening in a TM.

FIG. 9 is a longitudinal cross-section view of another example distal lens assembly that can be included as part of some embodiments of the surgical microscope system of FIG. 1.

FIG. 10 is a plan view from the perspective of the outer ear of another example distal lens assembly that can be included as part of some embodiments of the surgical microscope system of FIG. 1. The distal lens assembly is shown in position on a TM and includes a connected TM port device through which various types of instruments can be passed into the middle ear.

FIG. 15 is a schematic illustration of a medical procedure for visualizing a middle ear region using another example surgical microscope system in accordance with some embodiments.

FIG. 16 is a longitudinal cross-section view of the distal lens assembly of FIG. 15.

FIG. 17 is a proximal end view of the distal lens assembly of FIG. 15 with a peripheral structure for supporting the distal lens assembly within the outer ear.

Like reference symbols in the various drawings indicate like elements.

DETAILED DESCRIPTION OF ILLUSTRATIVE EMBODIMENTS

Figure 1:
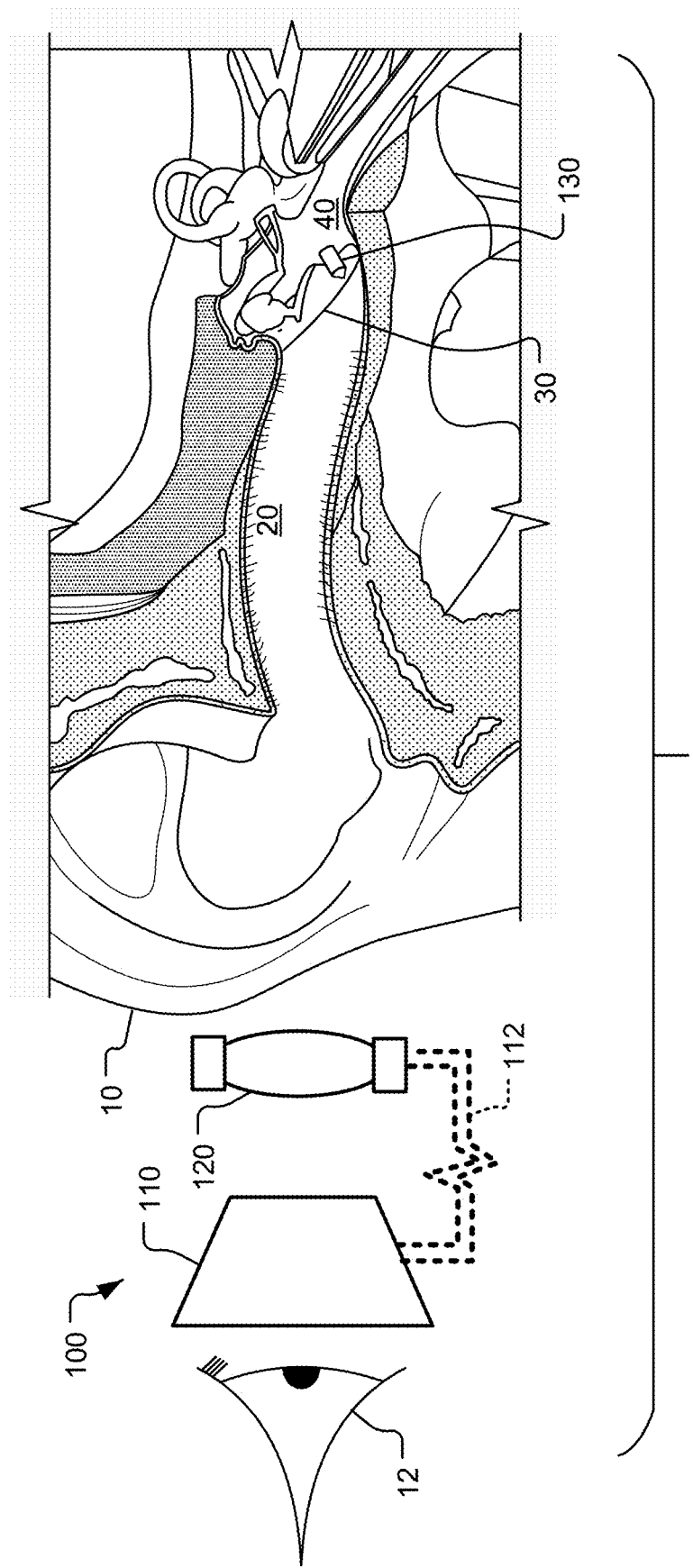
FIG. 1 is a schematic illustration of a medical procedure for visualizing a middle ear region using an example surgical microscope system in accordance with some embodiments.

Referring now to the schematic illustration of FIG. 1, particular embodiments of devices, systems, and methods for treating a patient 10 can include an example surgical microscope system 100. The surgical microscope system 100 can be used to facilitate viewing of structures in a recessed space such as, but not limited to, the middle ear 40.

In the depicted embodiment, the surgical microscope system 100 includes a surgical microscope 110 (and/or camera), a stereoscopic inverter lens system 120, and a distal lens 130. Images in the middle ear region 40 are captured by the distal lens 130 which, in this embodiment, is positioned in an opening in the TM 30. From the distal lens 130, the images are transferred to the stereoscopic inverter lens system 120 via the ear canal 20. The surgical microscope 110 receives the images from the stereoscopic inverter lens system 120 and presents them for viewing by the surgeon 12. The surgical microscope 110 allows binocular viewing or stereopsis, and largely hands free operation by the surgeon 12.

The stereoscopic inverter lens system 120 is external to the ear canal 20 in this embodiment. In some embodiments, the stereoscopic inverter lens system 120 is a prismatic inverter which can also be a stereoscopic diagonal inverter or stereo reinverter. This inverts the image to make it easier for the surgeon or clinician to correlate directionality of visualization to the object being viewed (e.g., moving an instrument to the right is viewed through the system as moving to the right). In particular embodiments, the stereoscopic inverter lens system 120 can include multiple portions such as a beam splitter, a stereo inverter, and objective lens, and so on.

In some embodiments, the surgical microscope system 100 includes a mounting 112 by which the stereoscopic inverter lens system 120 is adjustably mounted to the framework of the surgical microscope 110 (or camera). Accordingly, the stereoscopic inverter lens system 120 is alienable with the objective of the surgical microscope 110. Additionally, in some embodiments the mounting 112 can be adjusted to allow longitudinal adjustment.

Light for visualization using the surgical microscope system 100 can be externally provided through a light pipe or other source as described further below, or can be projected coaxially through the system. This surgical microscope system 100 has the advantage of allowing surgeons to use both hands during the treatment or diagnostic procedures, to have binocular viewing or stereopsis, and to be able to easily view down the ear canal 20 as typical with the surgical microscope. Further, the surgical microscope system 100 allows surgeons to easily switch to a widefield view within the middle ear 40 (e.g., to achieve view within view), while still having a large depth of focus and high resolution in the periphery. In addition, the surgical microscope system 100 allows surgeons to be able to pass instruments for the treatment or diagnostic procedures, as described further below, to still utilize surgical microscopes that surgeons are comfortable with, and to function in fluid-filled or air-filled spaces, among other advantages. This surgical microscope system 100 facilitates treatment methods and devices for treating the patient 10 using a minimally invasive approach.

While many of these example embodiments provided herein are described in combination or use with a surgical microscope, it is envisioned that the concepts also work well with digital viewing modalities or exoscopes. Digital viewing is well suited to displaying the image heads up on external monitors that can be high definition, 3D, curved, etc. Heads up viewing is also well suited to displaying picture-in-picture of the external ear canal simultaneously to showing, as an example, a wide-field view from the distal tip of one of the assemblies previously described. This would be surprisingly advantageous because it would enhance navigation of the assembly down the ear canal as well as passage of instruments down the canal, while simultaneously allowing a widefield view into the middle ear space (as an example).

When the concepts disclosed herein are used with digital viewing systems that enable heads up displays, the lens system embodiments can facilitate interactions with assisting personnel and training of new surgeons. Heads up displays, virtual reality ("VR"), 3D, and similar systems can dramatically improve ergonomics.

The systems and concepts described herein also work well in combination with navigation tracking and other robotic-assisted surgical modalities.

In some embodiments, the light source used with the systems described herein can be substituted from a typical visual spectrum source to infrared or other specific spectrum. Specific spectrums such as infrared can be useful on their own for tissue or vessel identification. Infrared is useful for identifying blood vessels and vasculature. The longer wavelength of infrared rays (>700 nm) are able to penetrate tissues more readily than visible light and could enable superior illumination of the middle ear through the tympanic membrane, where reflection and scattering of shorter wavelengths can be problematic. Fluorescent stains and other dyes or stains such as ICG are useful in combination with specific wavelength light sources, and/or specific filters, for identifying blood vessels and specific tissues. Examples are ICG-suitable (Indocyanine green; near infrared, with an excitation peak near 810 nm) for vessel identification and 5-aminolevulinic acid (5-ALA) or fluorescein for tumor identification. In the middle ear it would be particularly advantageous for these non-standard light sources to be used for identifying cholesteatoma or other soft tissue lesions that grow on top of bony structures, as an example.

FIGS. 2-10 illustrate various non-limiting examples of distal lenses 130. As depicted in some of the figures, the distal lens 130 allows visualization of the middle ear via the TM 30. Any of the distal lenses 130 can be configured to traverse the TM 30 (e.g., as illustrate in FIG. 5) and/or to be positioned adjacent to an opening in the TM 30 (e.g., as illustrated in FIG. 8).

The distal lenses 130 can be a simple or compound lens assembly, and can have widefield or wide angle lenses, zoom lenses, prismatic or reflector elements, condenser lenses, in isolation or in any combination. In some embodiments, the distal lens 130 is a lens with a prism element, either immediately adjacent or spaced out from the lens. One or more of the lenses that comprise the distal lens 130 can be biconvex, biconcave, planonvex, planoconcave, meniscus, achromatic, multilens, condensers, etc., in any combination. Lens that comprise the distal lens 130 can be constructed from materials such as, but not limited to, flint glass, hardened glass, polycarbonate, acrylic, or other materials, and combinations thereof. In some embodiments, lenses or assemblies that comprise the distal lens 130 can be injection-molded polymer optics. It will be beneficial to have the distal lens 130 made of disposable components to remove difficulties associated with sterilization and maintenance of lenses, as well as to reduce OR turnaround time. In some embodiments, the lenses includes a coating to reduce the potential for misting.

The distal lenses 130 can be made in a variety of sizes and focal lengths to accommodate the length of an individual patient's ear canal. For example, without limitation, three sizes could be made available for ear canal lengths of 19-23 mm, 23-27 mm, and 27-31 mm to maintain consistent microscope positioning for optimal instrument maneuverability and surgeon comfort.

Figure 2:
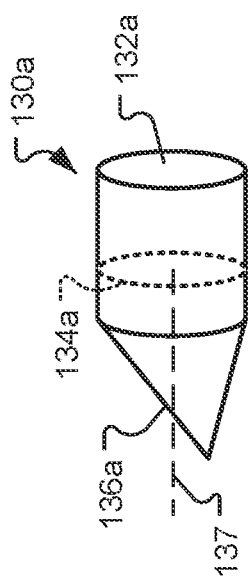
FIG. 2 illustrates an example distal lens assembly that can be included as part of some embodiments of the surgical microscope system of FIG. 1.

FIG. 2 shows an example distal lens assembly 130a. In the depicted embodiment, the distal lens assembly 130a has at its most distal end a widefield lens 132a, and then a 1-2 mm air gap to a zoom or objective lens 134a, and then a prism element 136a to redirect the proximally outgoing image angle, all mechanically coupled. The outer diameters of the lenses 132a and 134a can range from approximately 1 mm to 3 mm, or 1 to 5 mm, or 1 mm to 7 mm, or 3 mm to 8 mm, or 2 mm to 4 mm, or 3 mm to 6 mm, without limitation. These outer diameter dimensions can apply to any of the distal lens assemblies described herein. The prism 136a can have an approximately 42 degree angle (in relation to a central longitudinal axis 137 of the distal lens assembly 130a) to match the typical angle of the tympanic membrane relative to the predominant longitudinal axis of the ear canal.

In some embodiments, the angle of the prism 136a is in a range of about 40 degrees to 50 degrees, or 30 degrees to 60 degrees, or 20 degrees to 70 degrees, without limitation. These angular parameters can apply to any of the prisms described herein. The primary objective lens 134a can be part of the distal assembly 130a and can be for example a bi-convex lens (e.g., 60-120 D). For these example lenses in some cases it is preferable they are less than approximately 10 mm away from objects of interest.

Figure 3:
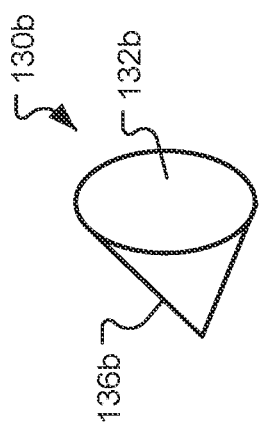
FIG. 3 illustrates another example distal lens assembly that can be included as part of some embodiments of the surgical microscope system of FIG. 1.

FIG. 3 shows another example distal lens assembly 130b. In the depicted embodiment, the distal lens assembly 130b has at its most distal end a widefield lens 132b, and then a prism element 136b to redirect the proximally outgoing image angle. In some embodiments, the size and other parameters of the distal lens assembly 130b can be the same as the distal lens assembly 130a.

Figure 4:
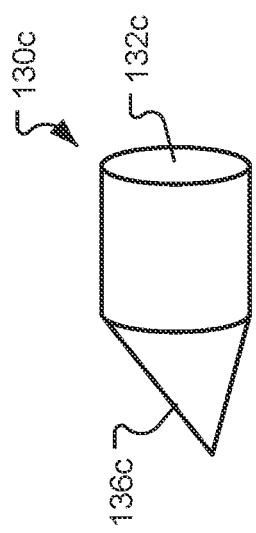
FIG. 4 illustrates another example distal lens assembly that can be included as part of some embodiments of the surgical microscope system of FIG. 1.

FIG. 4 shows another example distal lens assembly 130c. In the depicted embodiment, the distal lens assembly 130c has at its most distal end a widefield lens 132c, and then a 1-2 mm air gap, and then a prism element 136c to redirect the proximally outgoing image angle. In some embodiments, the size and other parameters of the distal lens assembly 130c can be the same as the distal lens assembly 130a.

Figure 5:
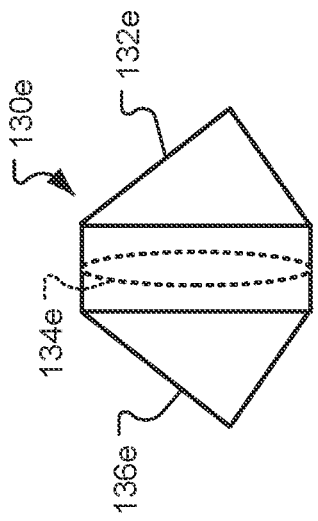
FIG. 5 illustrates another example distal lens assembly that can be included as part of some embodiments of the surgical microscope system of FIG. 1. The distal lens assembly is illustrated as traversing a TM.

FIG. 5 shows another example distal lens assembly 130d positioned penetrating the tympanic membrane 30. As depicted in this example, any of the distal lenses 130 described herein can have shape elements/features to facilitate maintaining the position of the distal lenses 130 in the TM 30 for the duration of a surgical or diagnostic procedure. Such elements can include having a waist portion 138d (or hourglass outer profile shape) that allows friction fit of the distal lenses 130 within an opening in the TM 30 and thereby provide longitudinal stability.

Any of the distal lenses 130 described herein can optionally include other elements to facilitate stabilization of the distal lenses 130 with respect to the TM 30. For example, the distal lenses 130 can include arm members, such as the arm members 139da and 139db as depicted in FIG. 5. Alternatively or additionally, the distal lenses 130 described herein can optionally include rings, interconnections with other elements, and/or other types of stabilization devices, without limitation. Moreover, in addition to stabilizing with respect to the TM 30 as shown, it is also envisioned that stabilization members of the distal lenses 130 described herein could stabilize against the ear canal wall, tympanic annulus, other instruments or access sites, and/or other adjacent structures. It can also be envisioned that these arm members 139da and 139db can be malleable or otherwise adjustable to allow fine-tuning of directionality and/or focus of the proximal "outgoing" image from any of the distal lenses 130 described herein.

Figure 6:
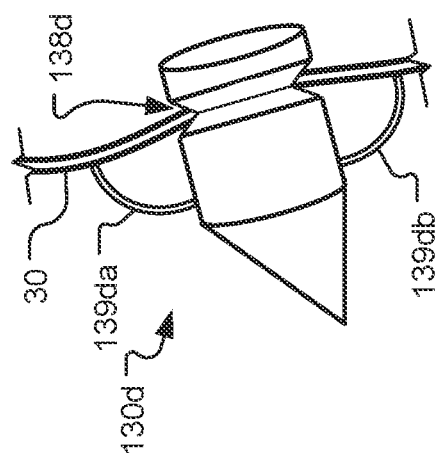
FIG. 6 illustrates another example distal lens assembly that can be included as part of some embodiments of the surgical microscope system of FIG. 1.

FIG. 6 shows another example distal lens assembly 130e with a distal prism member 132e, a zoom or objective lens 134e, and a proximal prism member 136e. The prism members 132e and 136e allow the visualization of an object distal to and off axis of the plane of the tympanic membrane, and the proximal image to be viewed off axis from the distal lens assembly 130e as described earlier.

FIG. 7 shows another example distal lens assembly 130f with a distal prism member 132f, a zoom or objective lens 134f, and a proximal prism member 136f In addition, the distal lens assembly 130f includes a lengthening member 133f to provide view at a depth inside the middle ear. Accordingly, the distal lens assembly 130f is a periscope-like distal lens assembly that, and the potential to see around typical structures in the middle ear that would block viewing directly through the tympanic membrane.

FIG. 8 shows the example distal lens assembly 130e situated over an opening 31 or other aperture in the TM 30. As an example, the opening 31 could be a puncture or an incision to the TM 30 made prior to situating the distal lens assembly 130e. In such an implementation, it can be envisioned that it would be especially advantageous to have arm members 139ea and 139eb (as shown), rings, or other stabilization devices to facilitate stabilization of the distal lens assembly 130e with respect to the surface or TM since the distal lens assembly 130e does not have the stabilization associated with penetrating the TM 30 (e.g., in contrast to the implementation depicted in FIG. 5, for example).

FIG. 9 shows another example distal lens assembly 130g. In this embodiment the proximal portion of the distal lens assembly 130g is a strong condenser lens 132g (e.g., approximately 60-130 D). In some embodiments, the diameter of the condenser lens 132g is about 3 mm. This proximal condenser lens 132g is mechanically connected to a port of a housing 134g that defines an interior chamber 133g between the strong condenser lens 132g and a distal-most lens 136g (which can be a plano lens, concave, convex, etc.). In some embodiments, the diameter of the distal-most lens 136g is about 2 mm.

In some embodiments, the interior chamber 133g can be air/gas filled or liquid filled and sealed. In some embodiments, and the interior chamber 133g itself can be a glass, polymeric, etc. The combination of the interior chamber 133g content and condenser lens 132g, and desired viewing outcome (e.g., such as degree of widefield and/or zoom) can dictate which distal-most lens 136g is most appropriate. The housing 134g can have a flange 135g or wings as example stabilization members to hold the distal lens assembly 130g consistently well-positioned in the TM.

FIG. 10 shows a top-down (or plan view) of the TM 30 (from the perspective of the outer ear) with another example distal lens assembly 130h positioned therein. The distal lens assembly 130h includes a lens portion 132h (which can be any of the types of distal lens assemblies described herein, and variations thereof). The distal lens assembly 130h also includes an integrated port 134h for passing instruments, lighting, therapeutics, needles, etc. through the TM 30 and into the middle ear. The lens portion 132h and the port 134h are coupled by a connecting member 136h which can be any suitable length. In some embodiments, two or more of the ports 134h can be included. In some embodiments, the distal lens assembly 130h can optionally include one or more fixation features to attach the distal lens assembly 130h to the fibrous tympanic annulus 32 for enhanced stability.

In the case where stabilizing features allow for a secure fit within the ear canal, the distal lenses 130 described herein could be implemented in surgical procedures where a tympanomeatal flap has already been created to provide widefield visualization directly into the middle ear cavity (e.g., not only "transtympanic" viewing). Similarly, it can be envisioned to use the distal lenses described herein in transmastoid procedures by having stabilization features that attach to structures (such as mastoid bone, canal wall, etc.) associated with establishing transmastoid access. In some embodiments, it can be envisioned having a stabilizing member that extends proximally out to the ear canal, outer ear, microscope, speculum, inverter, relay lens, or even to be hand held.

Figure 11:
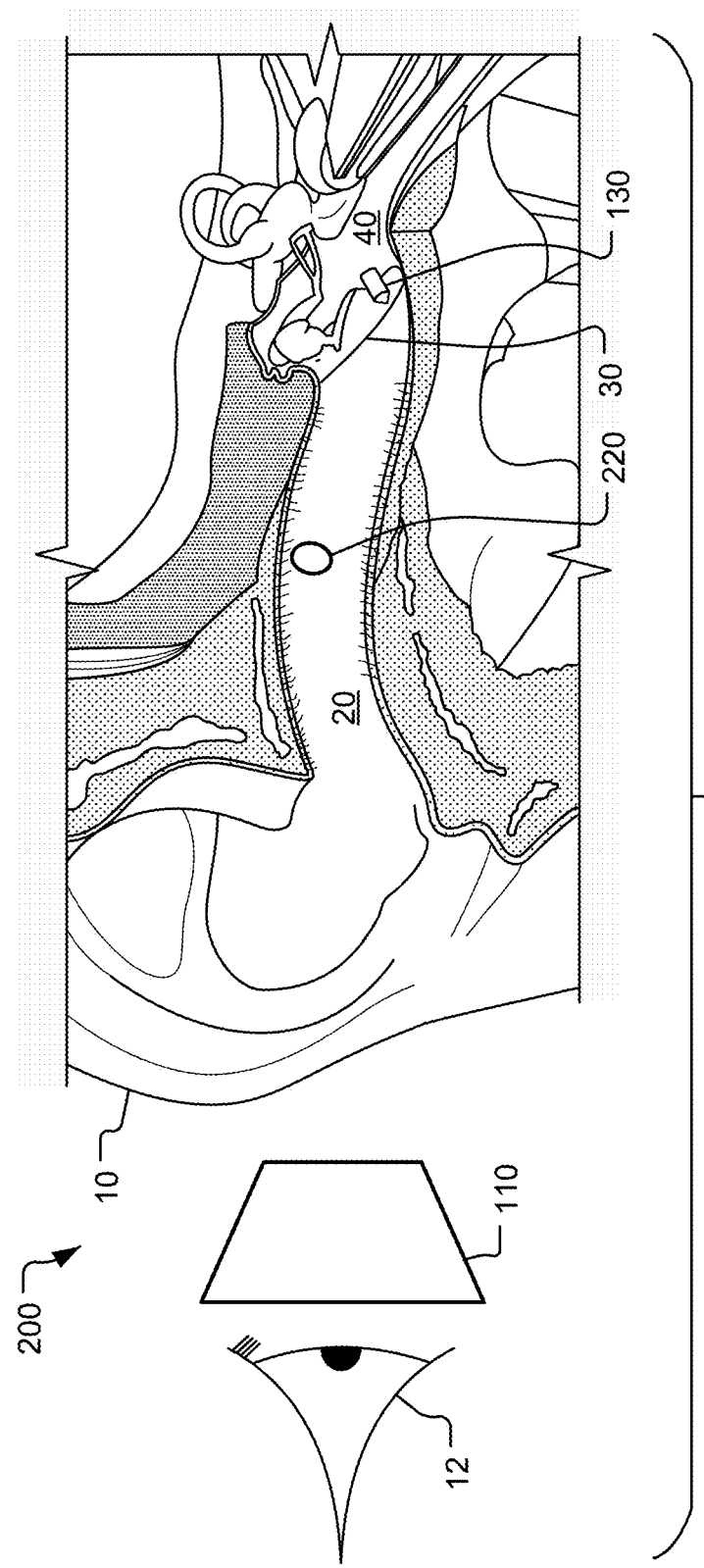
FIG. 11 is a schematic illustration of a medical procedure for visualizing a middle ear region using another example surgical microscope system in accordance with some embodiments.

FIG. 11 shows another surgical microscope system 200 that includes a surgical microscope 110 (and/or camera), a stereoscopic inverter lens system 220, and a distal lens 130.

Images in the middle ear region 40 are captured by the distal lens 130 which, in this embodiment, is positioned in an opening in the TM 30. From the distal lens 130, the images are transferred to the stereoscopic inverter lens system 220 via the ear canal 20. The surgical microscope 110 receives the images from the stereoscopic inverter lens system 220 and presents them for viewing by the surgeon 12. The surgical microscope 110 allows binocular viewing or stereopsis, and largely hands free operation by the surgeon 12. This schematic example shows that the stereoscopic inverter lens system 220 (which can include prisms and/or other lenses as necessary) can be situated at various locations within the outer ear 20, and that there can be zero, one, or more stereoscopic inverter lens systems 220. Image quality typically decreases with increasing number of lenses or prisms, so preferably there are as few as possible. Additionally, each stereoscopic inverter lens system 220 can reverse the image (depending on power) so the design of the stereoscopic inverter lens system 220 would be adjusted to compensate.

Figure 12:
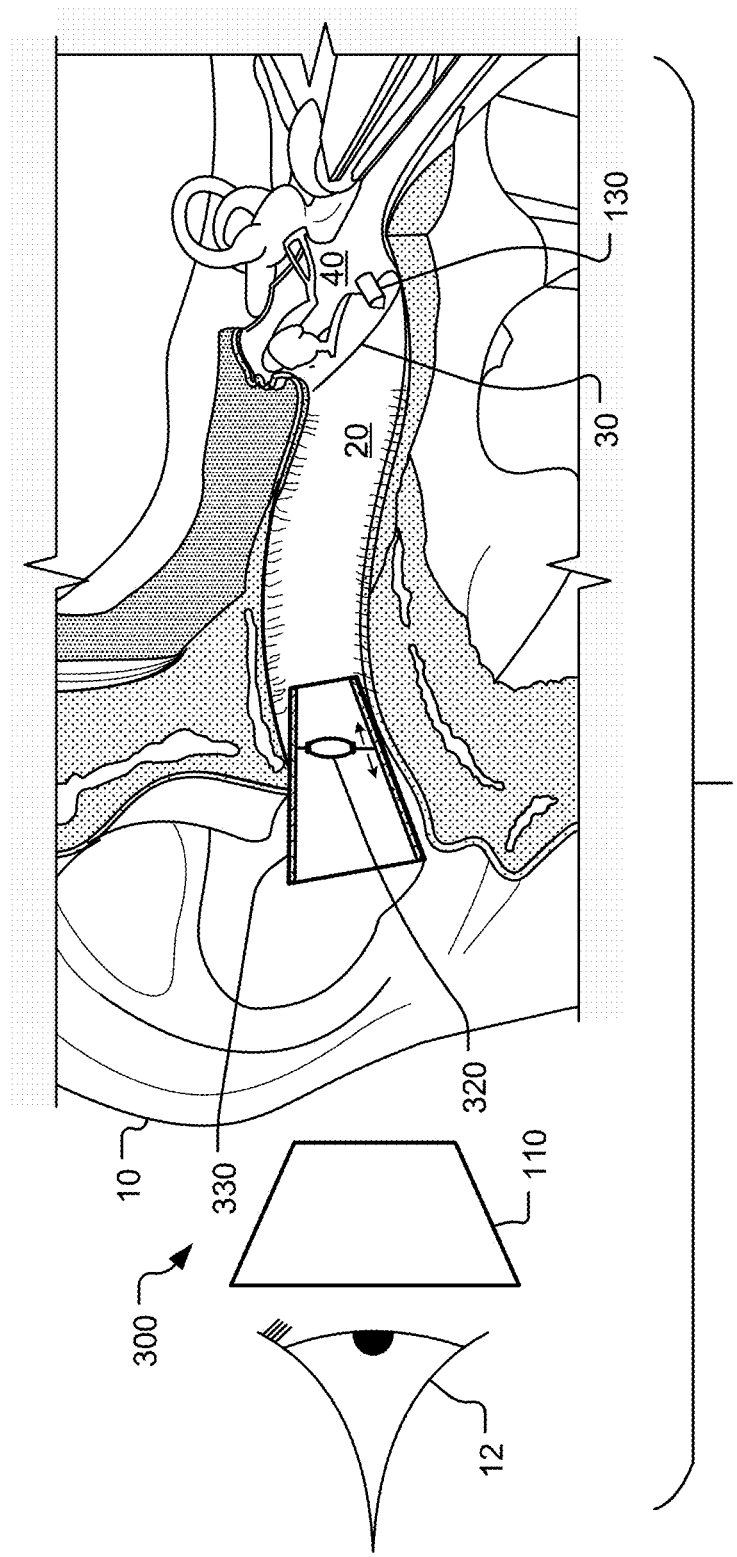
FIG. 12 is a schematic illustration of a medical procedure for visualizing a middle ear region using another example surgical microscope system in accordance with some embodiments.

FIG. 12 shows another surgical microscope system 300 that includes a surgical microscope 110 (and/or camera), a stereoscopic inverter lens system 320, and a distal lens 130. In the depicted embodiment, the stereoscopic inverter lens system 320 is mounted to a speculum 330 or external ear stabilizer. The stereoscopic inverter lens system 320 can be situated in the center of the speculum 330 or stabilizer, or mounted off-center or to one side.

In some embodiments, arm members, features, or anchors can mechanically couple the stereoscopic inverter lens system 320 to the speculum 300, and such features can be malleable or adjustable (as represented by the arrows) in order to align the alignment of the image from the stereoscopic inverter lens system 320 with the microscope 110 and/or the distal lens assembly 130. In some embodiments, the stereoscopic inverter lens system 320 can have multiple lenses or prisms in order to facilitate simultaneous alignment with the distal lens assembly 130 and the microscope 110 or camera, and as such the elements could be individually adjustable. In some embodiments, assembly 320 can be a relay lens and/or a prism. It can be appreciated that if stereoscopic inverter relay lens or prism lens system 320 is mounted to the speculum 330, that an inverter lens, if desired, may be mounted adjacent to the microscope 110.

Figure 13:
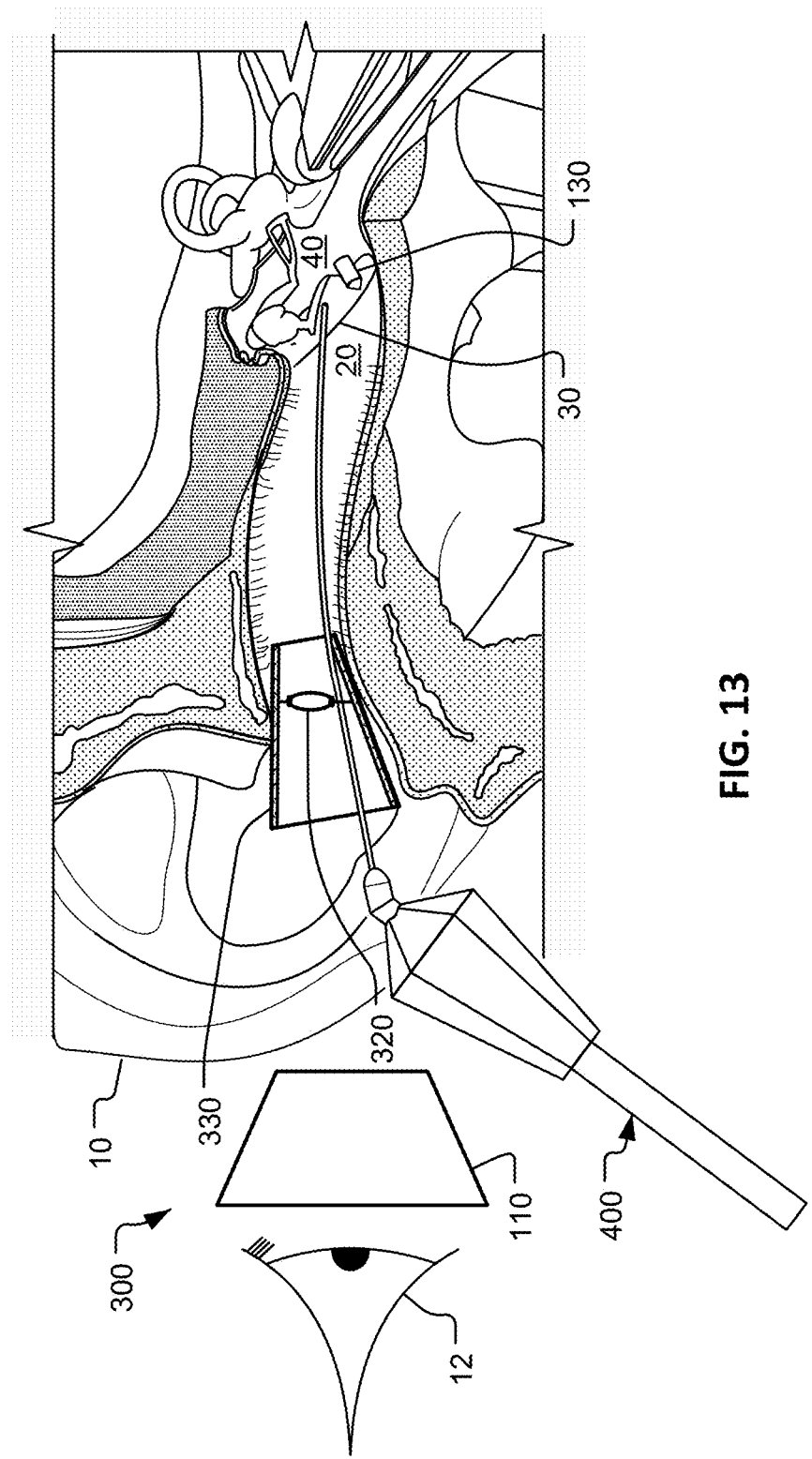
FIG. 13 illustrates the use of a surgical instrument in conjunction with use of the surgical microscope system of FIG. 12.

Referring also to FIG. 13, in some embodiments such arm members, features, or anchors that mechanically couple the stereoscopic inverter lens system 320 to the speculum 330 can provide sufficient lateral space or ports to allow simultaneous access for one or more instruments, delivery cannulas, light pipes, chandelier lighting, etc., to the outer ear 20, and through the TM 30 in some cases, and into the middle ear 40 in some cases (as broadly represented in FIG. 13 by the example instrument 400).

Additionally, in some embodiments a lighting source or element can be mounted to the speculum 330. In another embodiment, a light pipe is passed through the speculum 330 and is adjacent to the TM 30, or passed into the middle ear cavity 40. Chandelier lighting can be mounted to the TM 30. In some embodiments, the TM 30 can be treated with a solution, such as glycerol, to increase transparency and allow external lighting through the TM 30. In particular embodiments, the distal lens assembly 130 itself can have a light source attached to it (e.g., refer to FIG. 14), akin to what is seen on endoscopes.

In some embodiments, the light source would be distal to the most distal collecting lens 130 to minimize light scatter from the canal wall and other sources to stereoscopic inverter lens system 320. This would be ideally achieved through a chandelier light source distal to the TM 30 or via endo-illuminated instruments in the middle ear 40. Alternatively the stereoscopic inverter lens system 320 could be shielded within a tubular member with the light source positioned distal to the most proximal stereoscopic inverter lens system 320.

With appropriate middle ear illumination and enhanced transparency of the TM 30 (such as achieved with pretreated with glycerol, or saline solution, or refractive index matching material pretreatment), it can also be appreciated that the distal lens assembly 130 could be located proximal to the TM 30 without requiring an additional incision or opening in the TM 30. This would have the additional advantage of improved image stability with the distal lens assembly 130 anchored to the canal wall or external speculum such that movements of the TM 30 during instrument passage are not translated to the distal lens assembly 130. Using a fine (e.g., 25 gauge) or smaller fiberoptic light source, such a system could enable minimally invasive binocular office-based visualization of the middle ear 40 (currently not achievable) and enable a host of office-based procedures.

Figure 14:
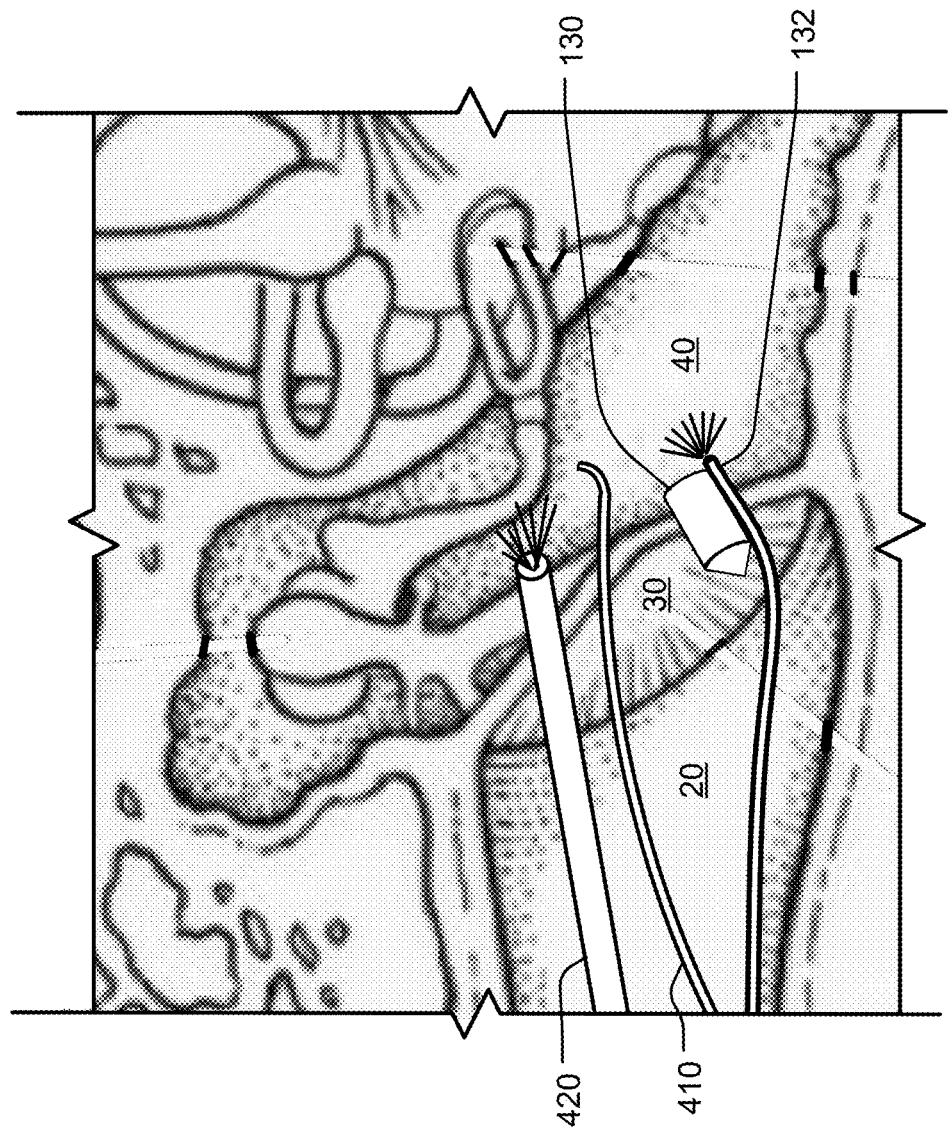
FIG. 14 illustrates the use of an example distal lens assembly, light source, and a surgical instrument in relation to a TM.

FIG. 14 shows a distal end portion of another implementation of a surgical microscope system in accordance with some embodiments. Namely, an example distal lens assembly 130 is shown in position traversing the TM 30. In the depicted embodiment, the distal lens assembly 130 includes an attached light pipe 132 that can illuminate the middle ear 40 and the anatomical structures in the region. Also shown for additional understanding is an example injector instrument 410 that can be passed through a port or opening in the TM 30. Such an injector instrument 410 can be used to deliver various therapeutic agents to various anatomical structures such as, but not limited to, the round window niche, the oval window, the walls or entrance of the mastoid antrum, soft tissue lesions, etc. Further, an example light pipe 420 is also depicted. Such a light pipe 420 can be passed through a port or opening in the TM 30, and can be used to illuminate the middle ear 40 and the anatomical structures in the region.

FIGS. 15-17 show another surgical microscope system 500 that includes a surgical microscope 110 (and/or camera), a stereoscopic inverter lens system 120, and a distal lens assembly 530. In the depicted embodiment, the stereoscopic inverter lens system 120 is residing external to the ear 10. The distal lens assembly 530 includes a tubular member that maintains the position and alignment between the distal lens assembly 530 and the stereoscopic inverter lens system 120.

FIG. 16 shows an example light path or ray tracing demonstrating a widefield view of an object at the distal end of the distal lens assembly 530, and output of an image at the proximal end of the distal lens assembly 530 that can be viewed through the surgical microscope 110. This approach would have the advantage of maintaining the light path alignment between the lenses and keeping instruments from interfering with visualization. It would also reduce interfering or stray light, and could have other features such as baffles, rod lenses, or others to improve image quality. A closed system or sealed assembly of the distal lens assembly 530 would have an additional advantage of minimizing fogging/fouling of the intermediate lens surfaces. It would also allow for procedures performed partially underwater where the distal lens assembly 530 is submerged and variable fluid level in the canal does not interfere with image or light transmission. Such a distal lens assembly 530 may also have a light source attached or integrated such that light is projected onto the object of interest, or light can be projected coaxially through the system.

This tubular embodiment of the distal lens assembly 530 may also have anchors, arm members 532, and/or other features to stabilize it in position in the outer ear 20 and to aid in alignment. For example, FIG. 15 shows an example arrangement of arm members 532 holding the tubular outer member or optic tube of the distal lens assembly 530 in place along the length of the ear canal 20.

FIG. 17 shows an end-on view of an example arm member embodiment of the distal lens assembly 530 with three arm members 532 extending radially from the distal lens assembly 530 in such a way to allow other instruments to pass by/through. It can be envisioned that there could be a port or other stabilizing feature to aid in passing through instruments without disturbing the optical tube, while also improving the stability of the instrument itself relative to the ear canal 20. In some embodiments, the arm members 532 can be fixably attached to a flexible ring 534 as an example way to minimize trauma or pressure on the wall of the ear canal 20. It can be envisioned that in some embodiments the arm members 532 are malleable or otherwise adjustable (such as being rotatably attached to the optical tube while having threaded sections that can be rotated within threaded portions of the flexible ring 534 such that rotating them shortens or lengthens the distance between the optical tube and flexible ring 534). The proximal end of the distal lens assembly 530 may end with a relay lens, prism, inverter, and/or the like.

Figure 18:
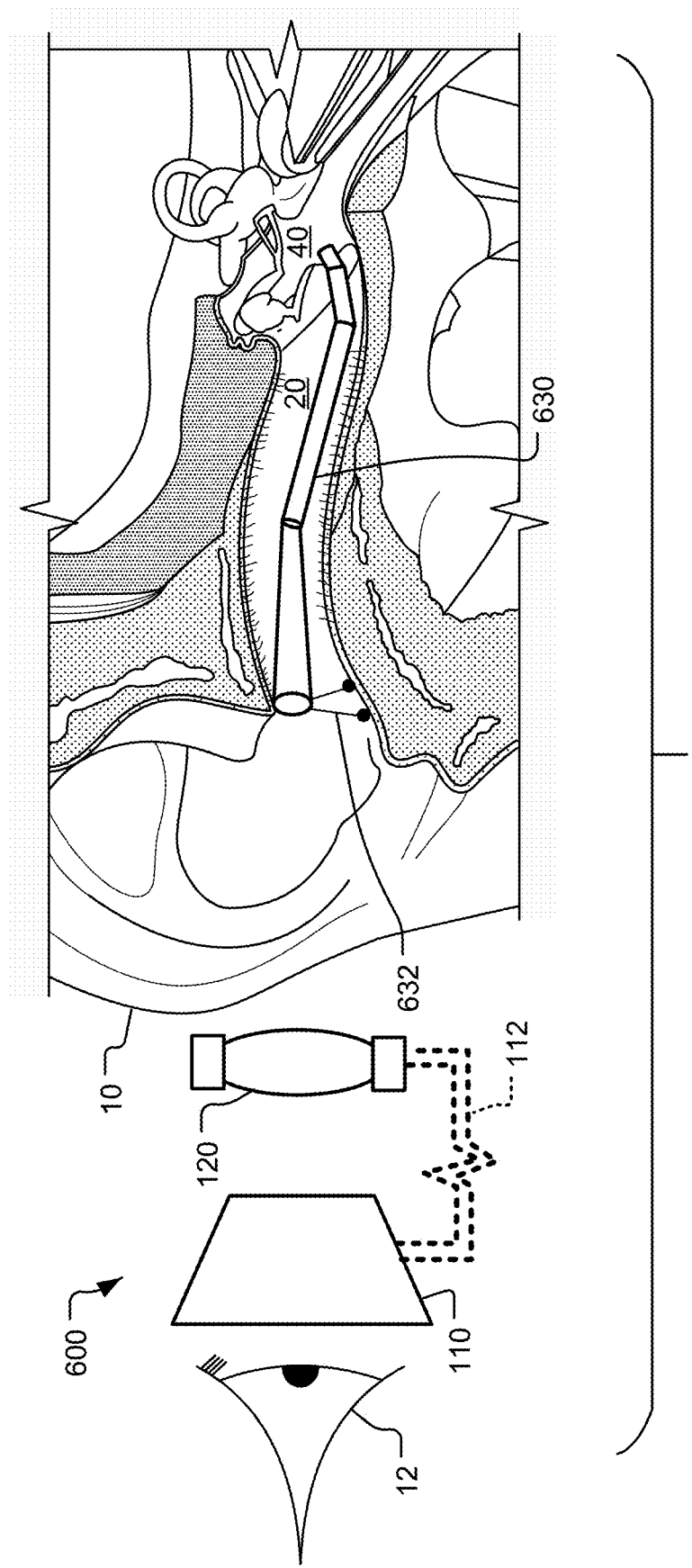
FIG. 18 is a schematic illustration of a medical procedure for visualizing a middle ear region using another example surgical microscope system in accordance with some embodiments.

FIG. 18 shows another surgical microscope system 600 that includes a surgical microscope 110 (and/or camera), a stereoscopic inverter lens system 120, and a distal lens assembly 630. In the depicted embodiment, the stereoscopic inverter lens system 120 is residing external to the ear 10. The distal lens assembly 630 includes a tubular member that maintains the position and alignment between the distal lens assembly 630 and the stereoscopic inverter lens system 120.

In the depicted embodiment, the distal lens assembly 630 includes an optical tube or outer tubular member that has multiple sections and relay lenses or prisms that allow angularity between the sections. In such an arrangement, the distal lens assembly 630 can include one or more intermediate relay lenses and can include prisms or other reflective members to compensate for the angularity between sections. Again, one or more arm members 632 can be used to stabilize or anchor the tubular member of the distal lens assembly 630 with respect to the wall of the ear canal 20. Such an embodiment, or other embodiments that can accommodate angularity in the light path, can be advantageous due to the frequent angularity encountered in situations such as trans-canal access.

Figure 19:
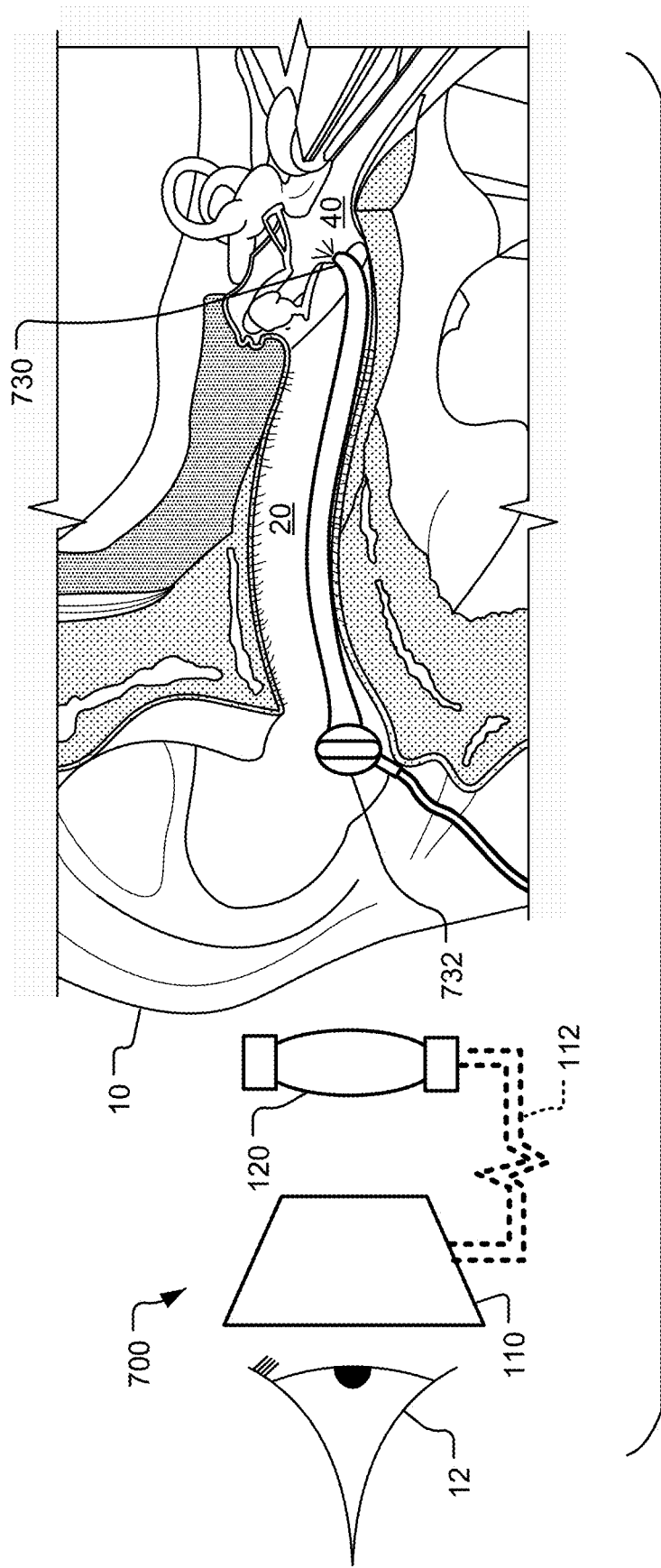
FIG. 19 is a schematic illustration of a medical procedure for visualizing a middle ear region using another example surgical microscope system in accordance with some embodiments.

FIG. 19 shows another surgical microscope system 700 that includes a surgical microscope 110 (and/or camera), a stereoscopic inverter lens system 120, and a distal lens assembly 730. In the depicted embodiment, the stereoscopic inverter lens system 120 is residing external to the ear 10.

The distal lens assembly 730 includes a tubular member that utilizes fiber optic fibers to "relay" the images from the distal end of the distal lens assembly 730 to a proximal lens 732, where the images can then be viewed by the surgical microscope 110 via the stereoscopic inverter lens system 120.

In some embodiments, the distal lens assembly 730 includes an integrated light source similar to a typical endoscope. In particular embodiments, the distal lens assembly 730 can be stabilized in place within the outer ear 20 using arm members or features as described above. Angulated assemblies such as this can potentially increase the space and degrees of freedom for more conventional straight-shafted or slightly curved instruments to pass towards the TM 30 laterally adjacent to the distal lens assembly 730.

While the instruments disclosed herein are primarily described in the context of otologic procedures that are either in the outer ear or that use a trans-canal trans-tympanic membrane approach to the middle ear or inner ear, it should be understood that the instruments are not limited to such uses, and could be used for other cavities or spaces in the body and other approaches. For example, in some embodiments the instruments described herein can be used for other approaches and techniques to the middle ear, inner ear, eustachian tube, mastoid antrum space including, but not limited to, trans-mastoid access, trans-canal via tympanomeatal flap, endaural, retroaural, postaural, and others. Such systems and methods can be used for drug delivery, gel delivery, antibiotic delivery, gene delivery, graft placement, device or implant delivery, tissue removal, diagnostic procedures, sampling procedures, surgical procedures, among others.

It should be noted that any of the embodiments or features of embodiments described herein can be combined in any combinations any permutations, and all are within the scope of this disclosure.

The devices, systems, and methods described herein may be used in the course of treating any disorder of the middle ear and/or inner ear including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, otitis media, middle ear infections, and tympanic membrane perforations, to provide a few examples. In some embodiments, the devices, systems, and methods described herein may be used in the course of precise delivery of therapeutic agents to the round window niche and/or other target sites, such as the oval window or other parts of the middle ear cavity, and for providing access to other features or regions of the middle ear. For example, the systems and methods described herein can be used for minimally invasive surgical reconstruction of the ossicular chain, for removal of cholesteatoma, for diagnostic assessment, and other procedures. Any and all such techniques for using the systems and methods described herein are included within the scope of this disclosure.

The devices and systems described herein may be constructed of metals such as but not limited to aluminum, stainless steel, etc., or of polymers such as but not limited to ABS, PEEK, PET, HDPE, etc., injection molded components, and so on. Components, such as the flexible rings can be constructed of elastomeric materials, gels, etc.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

A number of embodiments have been described. Nevertheless, it will be understood that various modifications may be made without departing from the claim scope here. Accordingly, other embodiments are within the scope of the following claims.

What is claimed is:

1. A surgical microscope system comprising:
    a surgical microscope;
    a stereoscopic inverter lens system positionable external to a tympanic membrane and being adjustably mounted to the surgical microscope; and
    a distal lens spaced apart from the stereoscopic inverter lens system and mountable within a portion of the tympanic membrane to facilitate visualization through the tympanic membrane and into a middle ear region, wherein the distal lens is positionable relative to the stereoscopic inverter lens system such that an image of the middle ear region captured by the distal lens is transferable to the stereoscopic inverter lens system external to the tympanic membrane for presentation at the surgical microscope.

2. The system of claim 1, wherein the distal lens comprises:
    a prism at a proximal end of the distal lens; and
    a widefield lens at a distal end of the distal lens.

3. The system of claim 2, wherein at least a portion of the stereoscopic inverter lens system is mounted within a speculum.

4. The system of claim 3, wherein the distal lens further comprises a zoom or objective lens disposed between the prism and the widefield lens.

5. The system of claim 4, wherein the distal lens comprises two or more stabilization arms extending radially outward from a body of the distal lens.

6. The system of claim 3, wherein the distal lens defines a waist having a smaller outer diameter than immediately adjacent proximal and distal portions of the distal lens.

7. The system of claim 3, wherein the distal lens includes a 1-2 mm air gap between the widefield lens and an objective lens, the objective lens being positioned between the widefield lens and the prism, wherein all of the widefield lens, the objective lens, and the prism are mechanically coupled together.

8. The system of claim 7, wherein the widefield lens and the objective lens each has an outer diameter of about 1 mm to 3 mm.

9. The system of claim 7, the prism has a proximal face that is angled relative to a central longitudinal axis of the distal lens at about 30 degrees to about 60 degrees.

10. The system of claim 3, wherein the portion of the stereoscopic inverter lens system mounted within the speculum is positionally adjustable with respect to the speculum.

11. The system of claim 3, wherein an open space is defined within the speculum and lateral of the portion of the stereoscopic inverter lens system mounted within the speculum.

12. The system of claim 3, further comprising a light pipe coupled to the distal lens.

13. The system of claim 3, wherein the distal lens includes an elongate tubular member and multiple lenses coupled to the tubular member to define a light path through the tubular member, and wherein the tubular member includes multiple sections that allow angularity between the sections.

14. The system of claim 3, wherein the distal lens includes an elongate tubular member enclosing fiber optic fibers configured to relay images from a distal end of the distal lens to a proximal lens of the distal lens.

15. The system of claim 1, wherein the distal lens comprises:
    a first prism at a proximal end of the distal lens;
    a second prism at a distal end of the distal lens; and
    a zoom or objective lens disposed between the first and second prisms.

16. The system of claim 1, wherein the distal lens comprises:
- a condenser lens at a proximal end of the distal lens and coupled to a housing; and
- a second lens at a distal end of the distal lens and coupled to the housing,
- wherein the housing defines an interior space between the condenser lens and the second lens.

17. The system of claim 16, wherein the housing includes a radially extending flange or arms.

18. A method for indirect viewing into a middle ear space of a patient, the method comprising:
- providing a surgical microscope system comprising:
  - a surgical microscope;
  - a stereoscopic inverter lens system; and
  - a distal lens:
- placing the distal lens in contact with a tympanic membrane of the patient; and
- viewing images of the middle ear space captured by the distal lens and relayed to the surgical microscope by the stereoscopic inverter lens system.

19. The method of claim 18, wherein the distal lens comprises:
- a prism at a proximal end of the distal lens; and
- a widefield lens at a distal end of the distal lens.

20. The method of claim 19, wherein the stereoscopic inverter lens system is external to an ear of the patient.

21. The system of claim 20, wherein said viewing comprises a hands free operation of the surgical microscope system.

22. The method of claim 21, wherein said viewing comprises binocular viewing of the middle ear space while using both hands free of surgical microscope system during a treatment or diagnostic procedure within the ear.

23. The method of claim 19, wherein the stereoscopic inverter lens system is within an ear canal of the patient.

24. The method of claim 19, wherein at least a portion of the stereoscopic inverter lens system is mounted within a speculum.

* * * * *